United States Patent [19]
Rossi et al.

[11] Patent Number: 6,100,087
[45] Date of Patent: Aug. 8, 2000

[54] RIBOZYMES TARGETED TO HUMAN CCR5 MRNA

[75] Inventors: John J. Rossi, Alta Loma; Laurence Cagnon, Duarte, both of Calif.

[73] Assignee: City of Hope, Duarte, Calif.

[21] Appl. No.: 09/038,741

[22] Filed: Mar. 11, 1998

[51] Int. Cl.[7] .............................. C07H 21/04; C12Q 1/68; C12H 15/00

[52] U.S. Cl. ........................ 435/320.1; 435/6; 435/91.31; 435/375; 435/455; 536/23.1; 536/23.2; 536/24.31; 536/24.33; 536/24.5

[58] Field of Search .......................... 435/6, 91.31, 325, 435/366, 440, 375, 372, 320.1; 800/137; 536/23.1, 23.2, 24.3, 24.5; 514/44

[56] References Cited

U.S. PATENT DOCUMENTS

| | | | |
|---|---|---|---|
| 5,496,698 | 3/1996 | Draper et al. | 435/6 |
| 5,525,468 | 6/1996 | McSwiggen | 435/6 |

FOREIGN PATENT DOCUMENTS

| | | |
|---|---|---|
| 9732019 | 9/1997 | WIPO . |
| 9745543 | 12/1997 | WIPO . |
| 9805798 | 2/1998 | WIPO . |
| 9817308 | 4/1998 | WIPO . |
| 9936518 | 7/1999 | WIPO . |

OTHER PUBLICATIONS

Branch TIBS 23:45–50, Feb. 1998.
Flanagen Nature Biotechnology 17:48–52, 1999.
Crooke, Ch 1 of Antisense Research & Applications, Springch, 1998, pp. 2–50.
Guignerd et al. J. of Immunology 160:985–992, Jan. 1998.
Combadiere et al. J. of Leukocyte Biology 60:147–152 (1996).
Bauer, G. et al., "Inhibition of Human Immunodeficiency Virus–1 (HIV–1) Replication after Transduction of Granulocyte Colony Stimulating Factor–mobilized CD34+ Cells from Hiv–1 Infected Donors Using Retroviral Vectors Containing Anti–HIV–1 Genes," *Blood*, vol. 89, Apr. 1, 1997, pp. 2259–2267.
Bertrand, E. et al., "The Expression Cassette Determines the Functional Activity of Ribozymes in Mammalian Cells by Controlling Their Intracellular Localization," *RNA*, vol. 3(1), 1997, pp. 75–88.
Taylor, N. R. et al., "Chimeric DNA–RNA Hammerhead Ribozymes Have Enhanced in vitro Catalytic Efficiency and Increased Stability in vivo," *Nucleic Acids Research*, vol. 20(17), Sep. 11, 1992, pp. 4559–4565.
Good, P. D. et al., "Expression of Small, Therapeutic RNAs in Human Cell Nuclei," *Gene Therapy*, vol. 4(1), 1997, pp. 45–54.
Rossi, J. J. et al., "Ribozymes as Anti–HIV–1 Therapeutic Agents: Principles, Applications, and Problems", *Aids Research and Human Retroviruses*, vol. 8(2), Feb. 1, 1992, pp. 183–189.
Gonzalez, M. et al., "A Hammerhead Ribozyme Targeted to the Human Chemokine Receptor CCR5", *Biochemical and Biophysical Research Communications*, vol. 251, Oct. 20, 1998, pp. 592–596.
Huang, Y. et al., "The role of a mutant CCR5 allele in HIV–1 transmission and disease progression", *Nature Medicine*, vol. 2, No. 11, Nov. 1996, pp. 1240–1243.
Liu, R. et al., "Homozygous Defect in HIV–1 Coreceptor Accounts for Resistance of Some Multiply–Exposed Individuals to HIV–1 Infection", *Cells*, vol. 86, Aug. 9, 1996, pp. 367–377.
Samson, M. et al., "Resistance to HIV–1 infection in caucasian individuals bearing mutant alleles of the CCR–5 chemokine receptor gene", *Nature*, vol. 382, Aug. 22, 1996, pp. 722–725.
Dragic, T. et al., "HIV–1 entry into CD4[+] cells is mediated by the chemokine receptor CC–CKR–5", *Nature*, vol. 381, Jun. 20, 1996, pp. 667–673.
Dean, M. et al., "Genetic Restriction of HIV–1 infection and progression to AIDS by a deletion allele of the CKR5 structural gene", *Science*, vol. 273, Sep. 27, 1996, pp. 1856–1862.
Deng, H. et al., "Identification of a major co–receptor for primary isolates of HIV–1", *Nature*, vol. 381, Jun. 20, 1996, pp. 661–666.

*Primary Examiner*—John L. LeGuyader
*Assistant Examiner*—Jane Zara
*Attorney, Agent, or Firm*—Rothwell, Figg, Ernst & Kurz

[57] ABSTRACT

This invention provides ribozymes and combinations thereof, to cleave RNA sequences. The invention also provides a method of treating HIV-1 by down-regulating the CCR5 receptor.

9 Claims, 9 Drawing Sheets

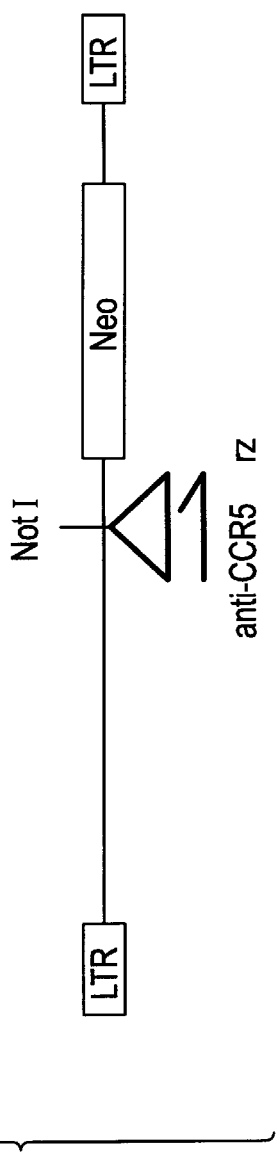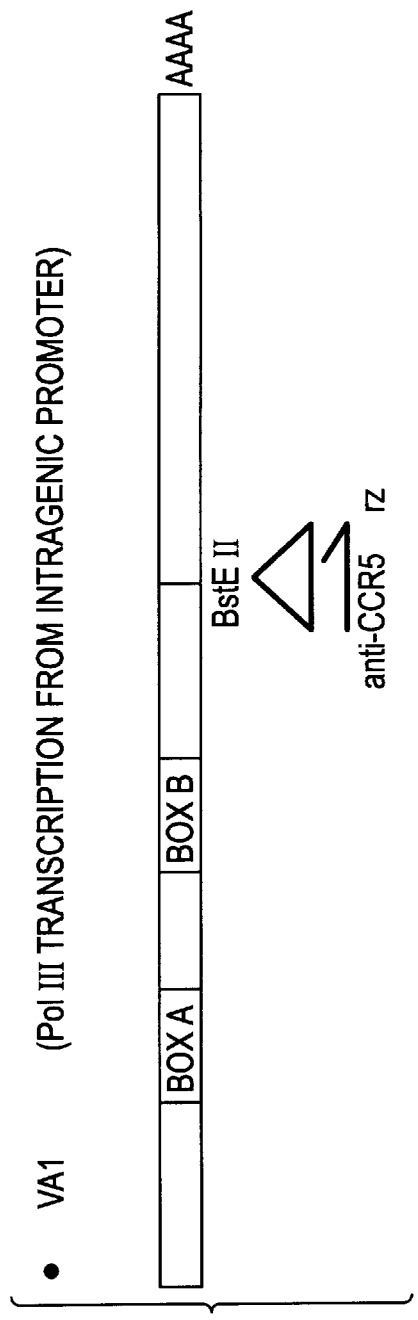
FIG. 8
FIG. 9

RIBOZYMES TARGETED TO HUMAN CCR5 MRNA

GOVERNMENT RIGHTS STATEMENT

This invention was made with government support under Grant No. AI 29329 awarded by the National Institutes of Health. The government has certain rights in the invention.

FIELD OF INVENTION

This invention relates to ribozymes and combinations thereof. More particularly, the invention broadly involves regulation of CCR5.

BACKGROUND OF THE INVENTION

The concept of genetic therapies for providing intracellular immunity to viral infection have been entertained for a number of years (see Baltimore, 1988; Szydalski, 1992). Gene therapy has recently received more attention for its potential utility in the treatment of HIV infection (Sarver and Rossi, 1993). A number of different inhibitory agents have been tested for their ability to confer resistance to HIV-1, including anti-sense RNA, ribozymes, TAR or RRE decoys, trans-dominant mutant HIV genes and conditionally lethal toxins (reviewed in Sarver and Rossi, 1993).

RNA-based strategies, such as anti-sense or ribozymes, have the dual advantage of being sequence specific, theoretically eliminating unwanted toxicities, as well as not producing potentially immunogenic proteins. A single ribozyme molecule is capable of irreversibly inactivating multiple target RNA molecules by sequential cycles of binding, cleavage and release. Even in the absence of multiple substrate turnover, ribozymes functionally inactivate target RNAs via cleavage (Zaug and Cech, 1986; Uhlenbeck, 1987; Castanotto et al., 1992).

Recently it has been discovered that individuals harboring a 32-base homozygous deletion in the CCKR-5 (also known as CCR5) gene are not subject to an infection by an M-tropic HIV-1 strain. Moreover, heterozygotes are long term survivors, which suggests that a defect in the CCR5 expression may interfere with the normal progression of AIDS. The protein encoded by the 32-based deletion gene is severely truncated, undetectable at the cell surface and with no obvious phenotype in homozygous individuals. This suggests that the inhibition of the CCR5 expression at the cell surface should affect the HIV-1 entry.

BRIEF DESCRIPTION OF DRAWINGS

FIG. 8 illustrates a RNA polymerase II expression system.

FIG. 9 illustrates a RNA polymerase III expression system.

SUMMARY OF THE INVENTION

Figure 1A:
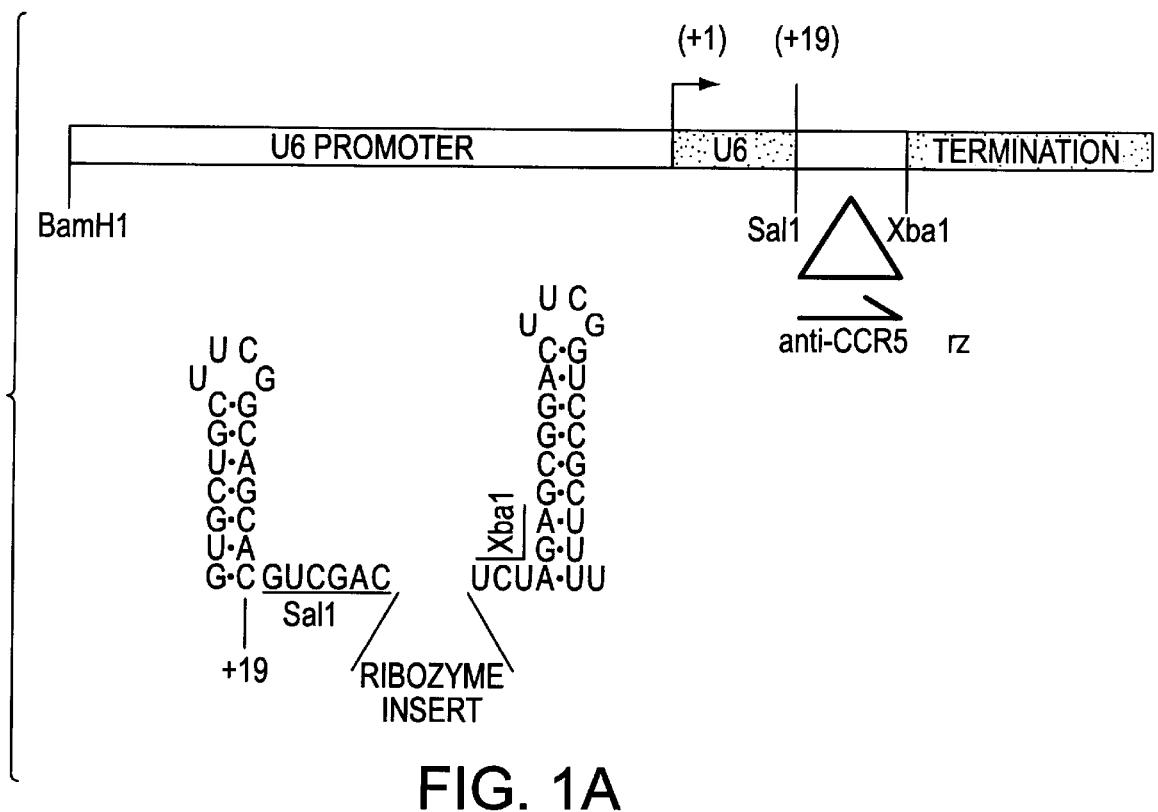
FIG. 1 is a schematic diagram indicating the U6 promoter construct used to transcribe an anti-CCR5 ribozyme.

This invention provides a method of treating HIV infection by down regulating CCR5 in mammalian cells. In other aspects, the invention provides novel ribozymes targeted against the CCR5 HIV-1 co-receptor.

The invention also provides a method of making HIV-resistant cells with vectors that express anti-CCR5 ribozymes. In preferred embodiments, the anti-CCR5 ribozyme is used in combination with one or more ribozymes targeted to conserved sequences in HIV.

DETAILED DESCRIPTION OF THE INVENTION

CCR5 is a seven transmembrane receptor for the beta-chemokines, MIP1-alpha, MIP1-beta and RANTES. Several studies have demonstrated the ability of these chemokines to inhibit HIV-1 infection of CD4+-T lymphocytes and to inhibit syncytia formation in HIV-infected cells. Individuals harboring a 32-base homozygous deletion in the CCR5 gene are not subject to infection by a M-tropic HIV-1 strain. Moreover, heterozygotes are long-term survivors, which raises the possibility that a defect in the CCKR-5 expression may interfere with the normal progression of AIDS. The protein encoded by the 32-based deletion gene is severely truncated, undetectable at the cell surface and with no obvious phenotype in homozygote individuals. Thus, it was hoped that the inhibition of the CCR5 expression at the cell surface would affect the HIV-1 entry, making downregulating CCR5 expression an attractive therapeutic approach for prevention and treatment of HIV-1 infection.

The present invention provides, among other features, a novel approach for downregulating CCR5 with ribozymes. The invention provides, in its various aspects, methods and compositions for altering the expression of the CCR5 receptor. Combinatorial vectors that express anti-CCR5 ribozymes, optimally in combination with one or more ribozymes targeted to conserved sequences in HIV, are used to transduce CD34+human hematopoietic precursor cells, which in turn will give rise to HIV resistant mononuclear cells.

A number of classes of catalytic RNAs (ribozymes) have been described in the literature, and the present invention is not limited to any one class of ribozyme. In a preferred aspect, however, the ribozymes of the present invention are "hammerhead" ribozymes. Such ribozymes have a hybridizing region (conferring the desired specificity) comprising one or more arms formed of single-stranded RNA having a sequence complementary to at least part of a target nucleic acid, such as mRNA. The hybridizing (or "anti-sense") regions comprise segments of RNA typically containing a sufficient number of nucleotides to effect hybridization to the target nucleic acid. Typically, these regions will contain at least about seven nucleotides, preferably from about nine to about twelve nucleotides. A conserved catalytic core region is capable of cleaving the targeted RNA. The preferred ribozymes of the present invention cleave target RNA which contain the sequence $X_1UX_2$ where $X_2$ is adenine, cytosine or uracil and U is uracil. Preferably, $X_1$ is guanidine, and $X_1UX_2$ is GUC or GUA.

The anti-sense arms of the ribozymes can be synthesized to be complementary to, and thus hybridizable to the RNA on the target CCR5 mRNA sequence flanking the chosen $X_1UX_2$ sequence. Upon hybridization of the anti-sense regions of the ribozyme to the target RNA sequence flanking the $X_1UX_2$ sequence, the catalytic region of the ribozyme cleaves the target RNA within the $X_1UX_2$ sequence. RNA cleavage is facilitated in vitro in the presence of magnesium or another divalent cation at a pH of approximately 7.5.

Figure 2A:
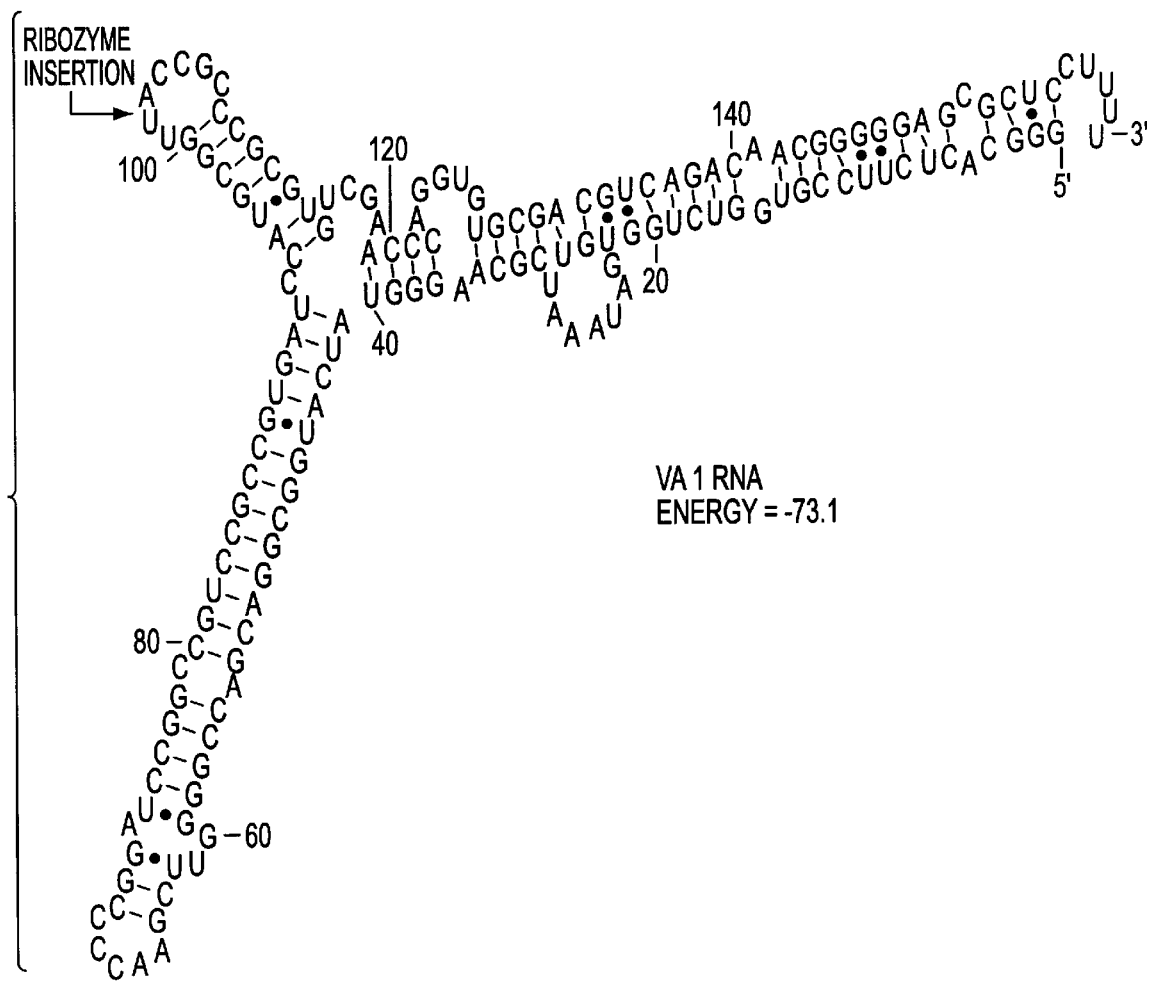
FIG. 2 illustrates the computer predicted secondary structure of VA1 (A) and VA1-anti-CCR5 ribozyme (B).
Figure 2B:
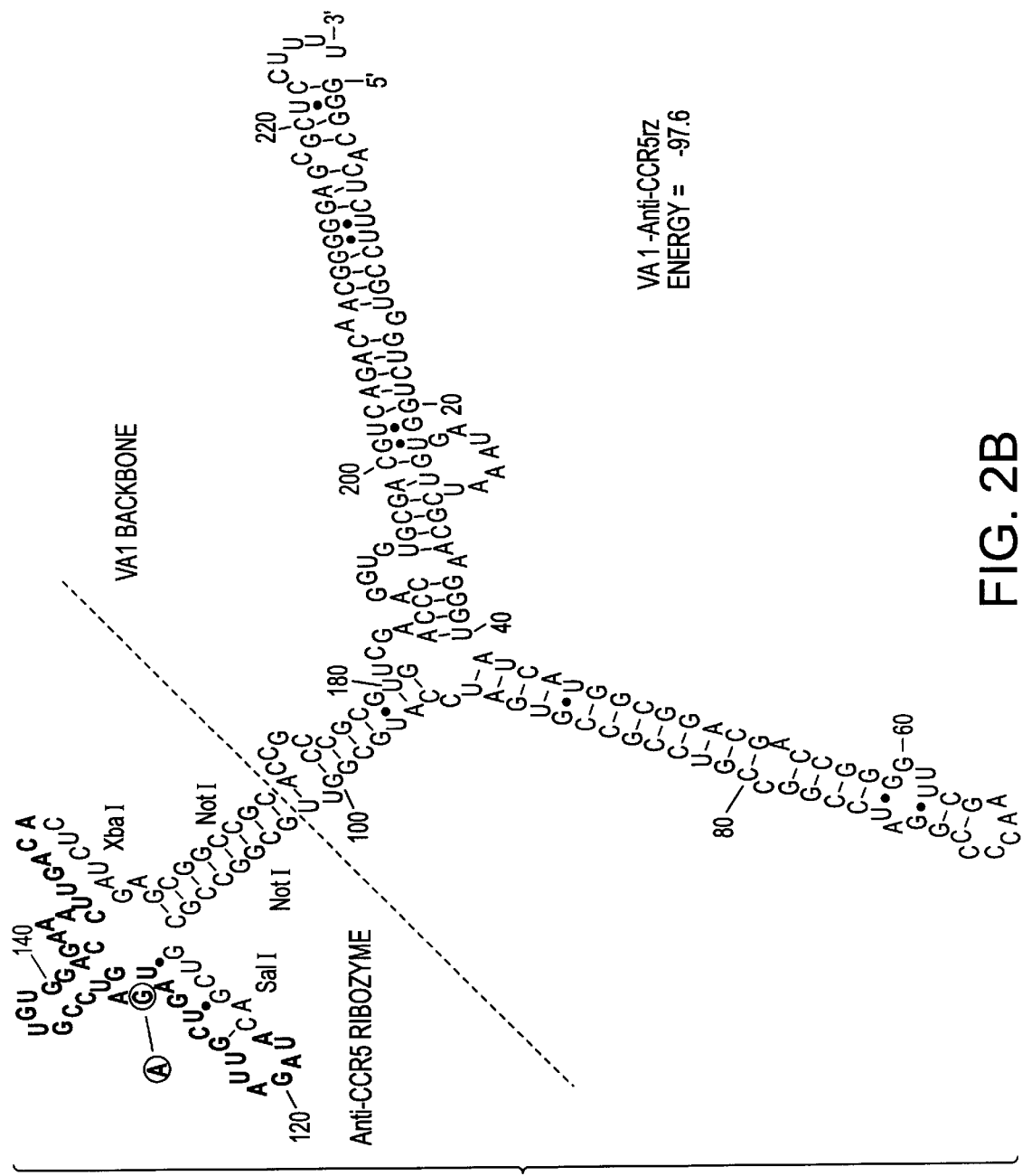
Figure 5:
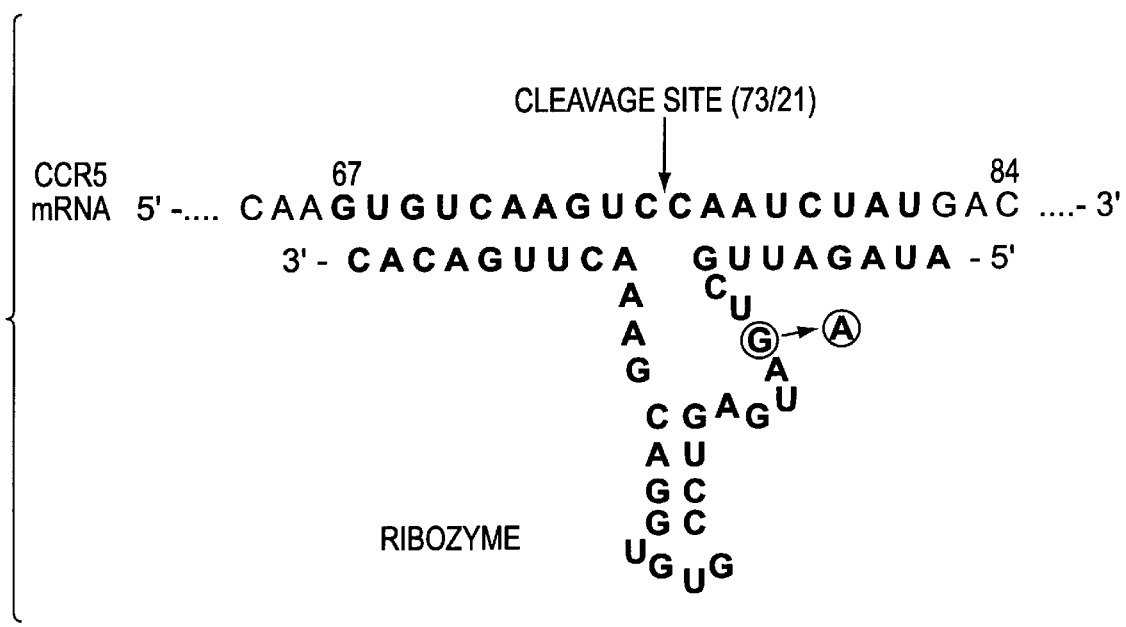
FIG. 5 illustrates an anti-CCR5 hammerhead ribozyme and target sequence.

In one embodiment of the invention, there is provided a hammerhead ribozyme as illustrated in FIG. 2. This ribozyme comprises a catalytic region having the sequence 3'-CACAGUUCAAAGCAGGUGUGCCUGAGUAGUCG UUAGAUA-5' (SEQ ID NO. 1) that recognizes a GUC sequence which is positioned immediately downstream of the CCR5 AUG initiation code. Specifically, the ribozyme targets against the second GUC of the CCR5 mRNA, from nucleotides 67 to 84 of the gene. The sequence in this region of the CCR5 mRNA is: 5'-GUGUCAAGUCCAAUCUAU-3' (SEQ ID NO. 2). Cleavage occurs after the C of the second GUC triplet (FIG. 5). The ribozyme interacts with its target by two short arms of 9 and 8 nucleotides each. To insure that this ribozyme does not target other members of the chemokine receptor family or other endogenous transcripts, the exact sequences from CCR5 which base pair with the ribozyme were entered in a BLASTN search of Genbank and no significant homology was found with any other essential gene.

Those skilled in the art will appreciate that the sequence of the ribozyme of FIG. 2 can be modified without departing from the invention. The catalytic region can be targeted to any $X_1UX_2$ sequence within the CCR5 mRNA, with the proviso that the $X_1UX_2$ sequence should be selected so as to result in the cleavage of the mRNA into one or more RNA strands that are incapable of serving as templates for the translation of a functional CCR5 molecule. Anti-sense regions capable of effectively bonding to bases (preferably 7–12 bases) upstream and downstream from the selected $X_1UX_2$ sequence will be selected based upon knowledge of the mRNA sequence.

The ribozymes can be further modified to include nuclease-resistant RNA bases. These modifications include, for example, the use of phosphorothioate derivatives of nucleotides (reviewed in Bratty et al., Biochem, Biophys. Acta 1216: 345–359 (1993)) To confer resistance to nucleases which degrade the ribozyme. The phosphorothioate group is introduced into the oligonucleotide using RNA or DNA polymerase and the corresponding nucleotide alpha-thiotriphosphate. Alternatively, the phosphorothioate group is inserted at specific positions and in oligomer as a phosphoramidite during chemical synthesis.

The ribozyme also can be synthesized in the form of a chimeric ribozyme containing deoxyribonucleotide as well as ribonucleotide bases. These chimeric ribozymes have been shown to have increased cellular stability while maintaining efficient cleavage properties. The chemistry of chimeric (DNA-containing) ribozymes (also known as "nucleozymes") is reviewed in Bratty et al. supra. For original article, see Taylor et al., Nucleic Acids RES., 20: 4559–4565 (1992).

Inasmuch as ribozymes act intracellularly the uptake of ribozymes by the targeted cells is an important consideration and advantageously is optimized. A preferred method for exogenous administration of a ribozyme is through the use of liposomes. Liposomes protect the ribozyme against enzymatic attack and the liquid capsule of the liposome facilitates transfer through the cell wall. Liposomes have been developed for delivery of nucleic acids to cells. See, e.g., Friedmann, Science, 244:1275–1281 (1989).

Direct cellular uptake of oligonucleotides (whether they are composed of DNA or RNA or both) per se presently is considered a less preferred method of delivery because, in the case of ribozymes and antisense molecules, direct administration of oligonucleotides carries with it the concomitant problem of attack and digestion by cellular nucleases, such as the RNAses. One preferred mode of administration of anti-CCR5 ribozymes takes advantage of known vectors to facilitate the delivery of a gene coding for the desired ribozyme sequence such that it will be expressed by the desired target cells. Such vectors include plasmids and viruses (such as adenoviruses, retroviruses, and adeno-associated viruses) [and liposomes] and modifications therein (e.g., polylysine-modified adenoviruses [Gao et al., Human Gene Therapy, 4:17–24 (1993)], cationic liposomes [Zhu et al., Science, 261:209–211 (1993)] and modified adeno-associated virus plasmids encased in liposomes [Phillip et al., Mol. Cell. Biol., 14:2411–2418 (1994)]. Expression of ribozyme RNA is driven by genetic elements such as RNA polymerase II and III.

The ribozymes of the present invention may be prepared by methods known in the art for the synthesis of RNA molecules. In particular, the ribozymes of the invention may be prepared from a corresponding DNA sequence (DNA which on transcription yields a ribozyme, and which may be synthesized according to methods know per se in the art for the synthesis of DNA) operably linked to a promoter. The DNA sequence corresponding to a ribozyme of the present invention may be ligated into a DNA transfer vector, such as a plasmid, bacteriophage DNA or viral DNA. Procaryotic or eukaryotic cells (including mammalian implanted cells) may then be transfected with an appropriate transfer vector containing genetic material corresponding to the ribozyme in accordance with the present invention, operably linked to a promoter, such that the ribozyme is transcribed in the host cell. Ribozymes may be directly transcribed from a transfer vector, or, alternatively, may be transcribed as part of a larger RNA molecule which then may be cleaved to produce the desired ribozyme molecule. While various methods of transforming cells so as to produce the desired ribozyme are described herein, those skilled in the general field of non-native (recombinant) gene expression in mammalian cells will apply known techniques to provide additional means and methods for providing or optimizing ribozyme expression in CCR5 producing cells.

Figure 1B:
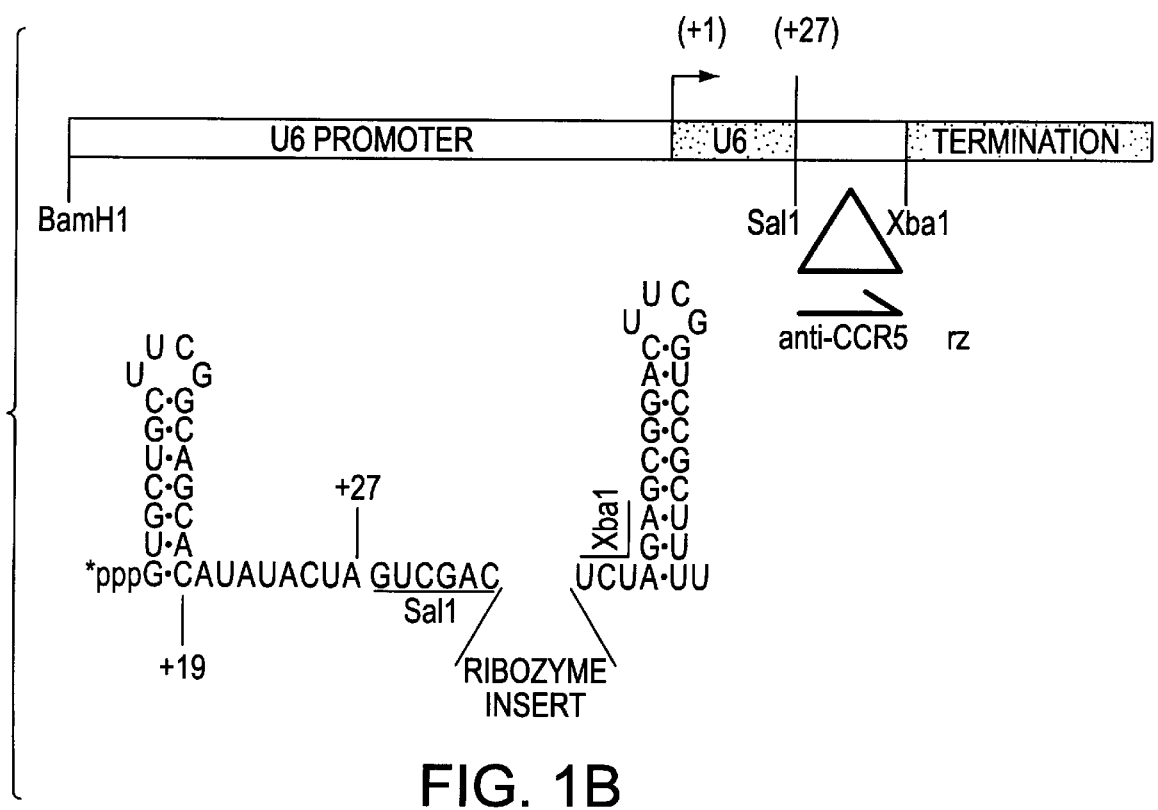
Figure 3A:
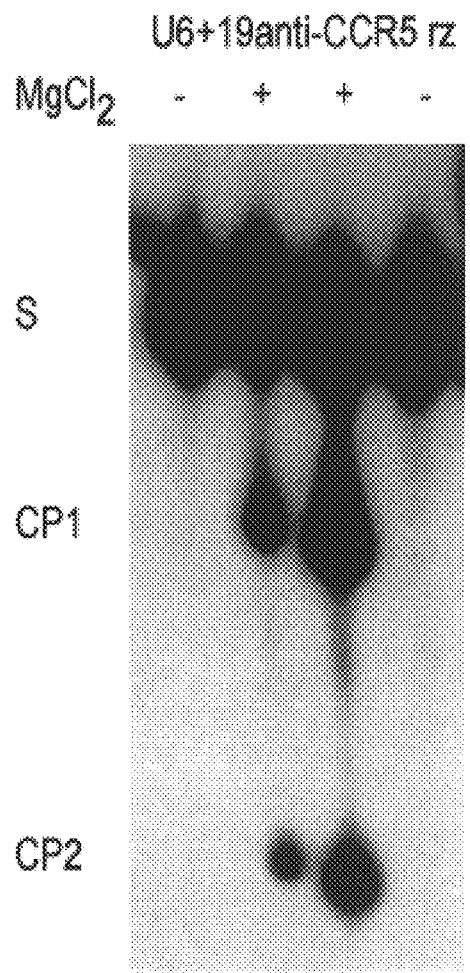
FIG. 3 is an in vitro ribozyme cleavage reaction comparing U6+19-CCR5 ribozyme and U6+27-CCR5 ribozyme.
Figure 3B:
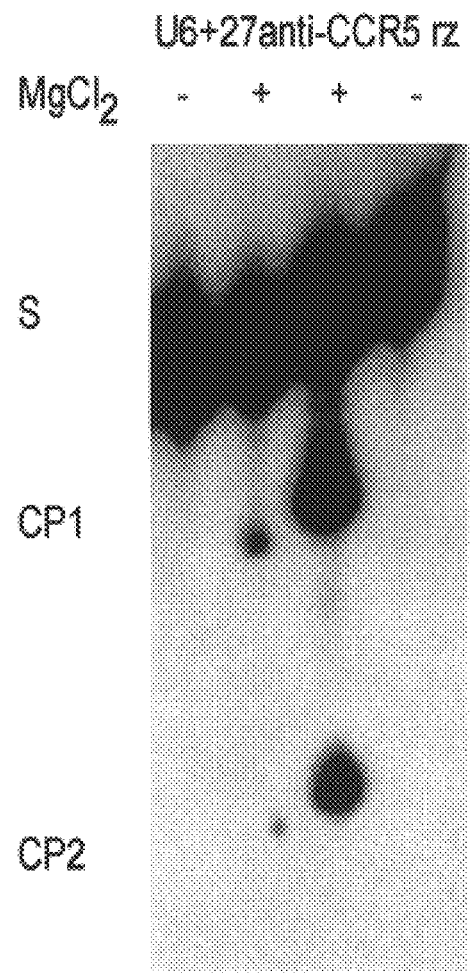

The ribozyme encoding sequence of FIG. 5 has been chemically synthesized and cloned into four different expression vectors. The first two vectors are derived from the human U6 gene described in Bertrand et al. 1997 and Good et al., 1997 (FIG. 1). This is a Pol III cassette in which the promoter is 5' to the transcribed sequences. The difference between the two constructs resides in the amount of U6 sequence included in the RNA transcripts. The first 19 bases of this RNA (U6+19, SEQ ID NO. 3) form a stabilizing stem-loop (Bertrand et al., 1997), but lack information for capping (FIG. 8). The additional eight bases included in the U6+27 (SEQ ID NO. 4) result in capping of the RNA with a gamma methyl phosphate (Singh, Gupta and Reddy, 1990; Goode et al., 1997) (FIG. 9). The U6+19, although primarily nuclear, can also be found in the cytoplasma to varying degrees (Bertrand et al., 1997), whereas the U6+27 sequence is exclusively nuclear. Advantageously, a stabilizing 3' stem-loop structure (SEQ ID NO. 5) that is transcribed in both of these promoter cassettes may be appended to the ribozyme sequence. In order to evaluate the relative cleavage activities of the ribozymes with the appended 5' and 3' sequences, RNAs from both the U6+19-CCR5 and U6+27 CCR5 ribozyme cassettes were prepared using PCR. These ribozymes were prepared from a PCR generated transcriptional template which utilizes the bacteria phage T7 promoter. The transcripts produced mimic exactly (with the exception of the cap on U6+27) those that would be transcribed from the U6 promoter. The in vitro cleavage reactions mediated by these two different RNAs are shown in FIG. 3. The U6+19 and U6+27 appended ribozymes cleave the CCR5 target with the same apparent efficiencies.

Figure 6:
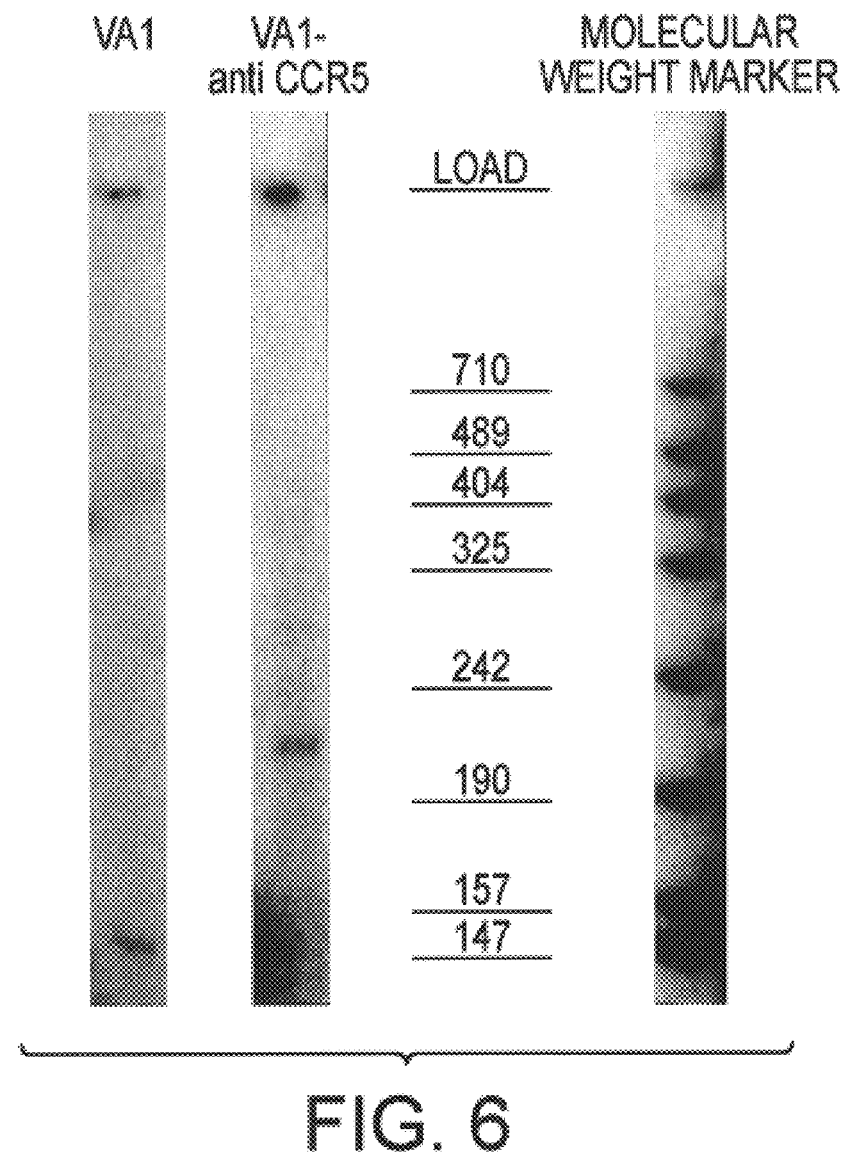
FIG. 6 depicts detection of VA1 and VA1-CCR5rz RNA in transiently transfected cells.
Figure 7:
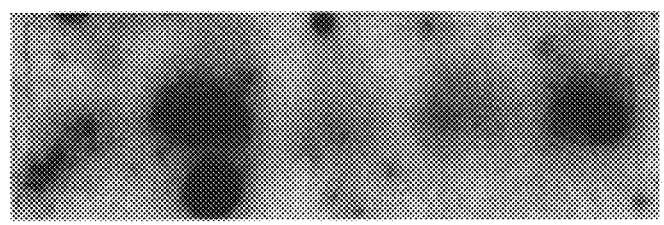
FIG. 7 is a northern blot from 293 cells transfected with pVA1 (lane 1), pVA1 anti-CCR5 ribozyme (lanes 2 and 3), and pVA1 anti-CCR5 ribozyme mutant (lanes 4 and 5).

Two other promoters tested for functional expression of the anti-CCR5 ribozyme were the MoMLV LTR promoter (in an LN retroviral vector) and the adenoviral VA1 promoter (FIGS. 6 and 7). The MoMLV promoter construct provides a cap and poly A sequence on the ribozyme transcript and has been used successfully to transcribe anti-tat and tat/rev ribozymes in both cell culture studies and in preclinical trials (Zhou, et al., 1994; Bertrand et al, 1997; Bauer et al., 1997). The Adenoviral VA1 promoter, which is a Pol III promoter generates a cytoplasmically localized RNA (SEQ ID NO. 6). Like most Pol III promoters and unlike the U6 promoter, the control regions are internal to the coding sequence. An advantage of this system is that the VA sequences impart a highly stabilized structure which can be very long-lived in the cytoplasm. Shown in FIG. 2 is the computer-predicted, thermodynamically most stable structure for the VA1-CCR5 ribozyme (SEQ ID NO. 4). By inserting the ribozyme at the top of the stem loop structure, the ribozyme structure is maintained. The VA1-CCR5 ribozyme construct pictured in FIG. 2 has been tested in vitro for ribozyme cleavage activity. The entire VA1-CCR5 ribozyme RNA was transcribed in vitro using bacteriophage T3 polymerase mediated transcription from a linearized DNA template. It can be seen from the data in FIG. 4 that despite being sequestered in VA1 RNA this ribozyme can cleave the CCR5 substrate.

The invention is further illustrated by the following examples, which are not intended to be limiting.

EXAMPLE I

U6+19 CCR5rz and U6+27 CCR5rz in Vitro Cleavage Reactions.

A radiolabelled 103-nucleotide CCR5 target (s) was incubated in the presence of ribozyme at 37° C. under the conditions described below (FIG. 3). The cleavage reaction products were analyzed on a 6% polyacrylamide, 7M urea denaturing gel. Panel A shows the in vitro cleavage reaction of the radiolabelled 103-nucleotide CCR5 substrate (S) by the U6+19 CCR5rz, at 37° C., in presence (+) (lane 2 and 3) or absence (−) (lanes 1 and 4) of 20 mM Magnesium, and at times 5 minutes (lanes 1 and 2) or 1 hour (lanes 3 and 4).

Panel B shows the results of the in vitro cleavage reaction of a radiolabelled 103 nucleotide CCR5 substrate (S) by the U6+27 CCR5rz, at 37° C., in presence (lane 2 and 3) or absence (−) (lanes 1 and 4) of 20 mM Magnesium, and at times 5 minutes (lanes 1 and 2) or 1 hour (lanes 3 and 4).

The cleavage products are respectively 72 (CP1) and 31 (CP2) nucleotides. Ribozyme and substrate are respectively at a 5:1 ratio.

EXAMPLE II

VA CCR5rz and VACCR5rzm in Vitro Cleavage Reactions.

Figure 4:
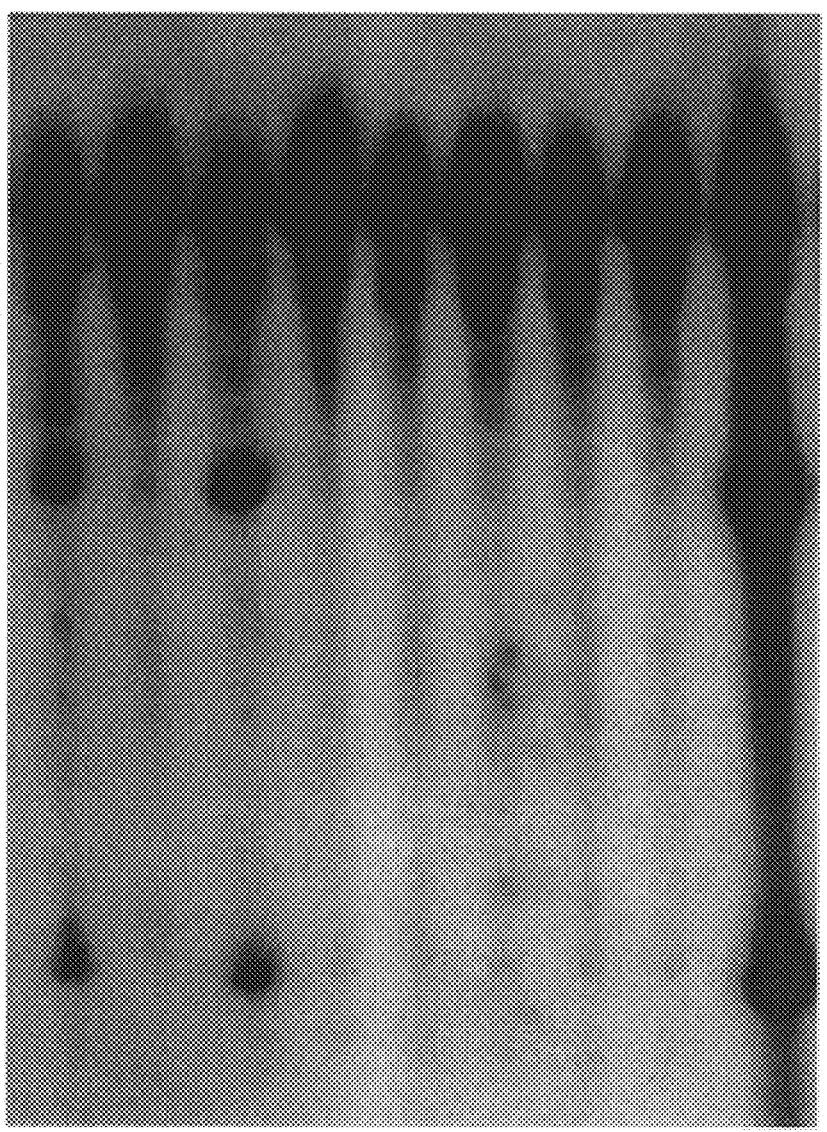
FIG. 4 is an in vitro ribozyme cleavage reaction using VA CCR5rz and VACCR5rzm with the CCR5 substrate.

A radiolabelled 103 nucleotide CCR5 target (S) was incubated in presence of the V Arz 1 and 2 (different preparations of the same ribozyme construct) (FIG. 4, lanes 1–4) or the crippled version, V Arzm1 and 2 (FIG. 4, lanes 5–8), in presence (+) or absence (−) of 20 mM MgC12, for 2 hours at 37° C. The cleavage reaction was then analyzed on a 6% polyacrylamide, 7M urea denaturing gel and the results are shown in FIG. 4.

The cleavage products are respectively 72 (CP1) and 31 (CP2) nucleotides. Ribozyme and substrate are respectively at a 5:1 ratio.

Lane 9 represents cleavage with the U6+27 CCR5 ribozyme used as a positive control (same reaction as in FIG. 3, panel B, lane 3).

EXAMPLE III

Detection of VA1 and VA1-CCR5rz RNA in Transiently Transfected Cells.

RNA analysis was performed by primer extension on the RNA from transiently transfected 293 cells (FIG. 6). The 293 cells were tranfected by either the VA1 plasmid or the VA1-anti-CCR5 plasmid. Two days after the transfection, the RNAs were prepared and used for primer extension with a probe specific to the 3' end of the VA1 RNA.

EXAMPLE IV

Northern Blot From 293 Transiently Transfected Cells.

RNA from 293 cells transfected with pVA1 (lane 1), pVA1 anti-CCR5 ribozyme (lanes 42 and 3) and pVA1 anti-CCR5 mutant (lanes 4 and 5) (FIG. 7). The probe used was specific for the 3' end of the VA1 RNA.

EXAMPLE V

Down-regulation of CCR5 Receptor in Cell Culture.

HOS-CD4-CCR5 cells were obtained from the National Institutes of Health, Bethesda, Md., U.S.A. These cells were transiently transfected (lipofection) with the various constructs described in Examples I and II. Forty-eight hours after the transfection, a binding assay was performed with the iodinated ligand MIP-1β.

Figure 10:
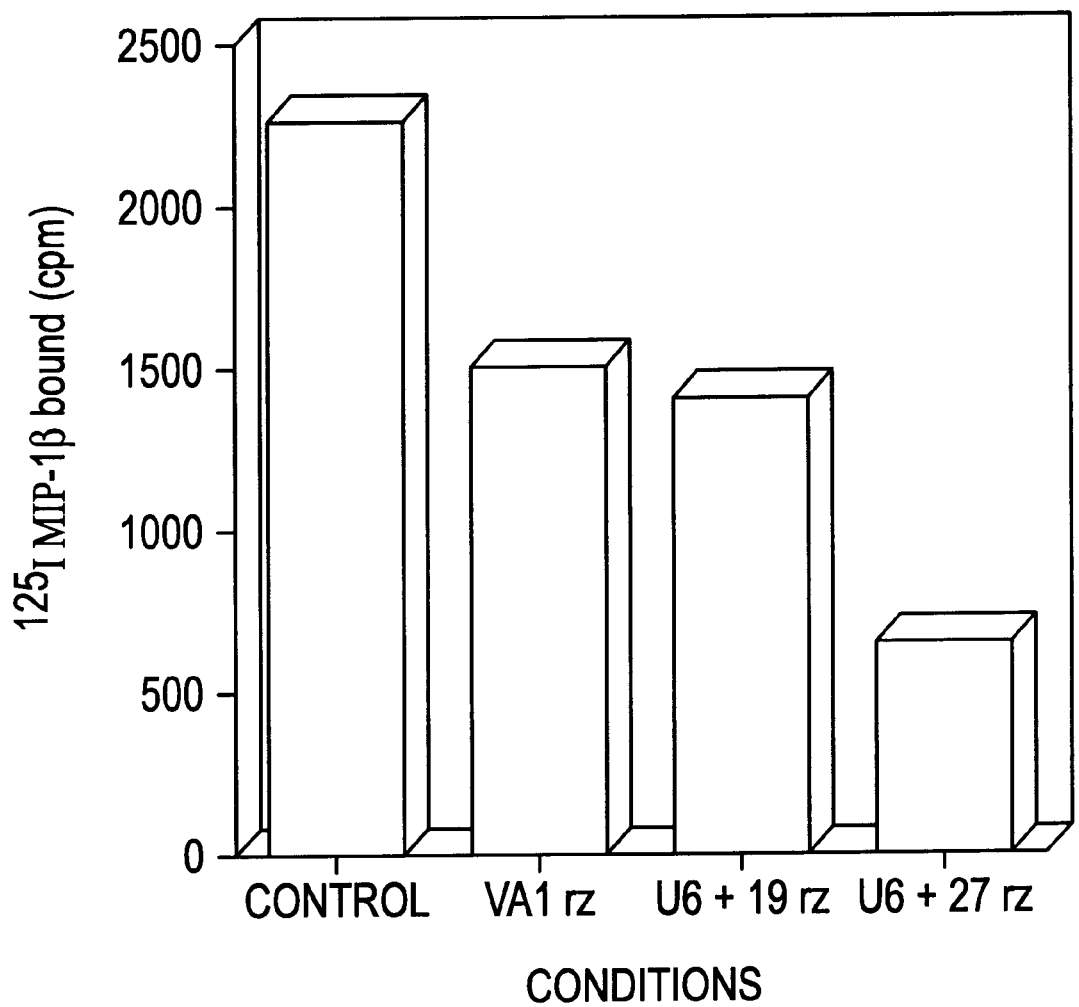
FIG. 10 is a graph depicting down regulation of CCR5 receptor in cell culture.

The cells were incubated at 4° C., with 1 nM of $^{125}$I-MIP-1β for 2 hours, in presence or absence of 100 nM of unlabelled MIP-1β. The cells were then washed 3 times with phosphite-buffered saline and the cell pellets counts were evaluated. The background counts were measured in the presence of the 100 fold excess of cold ligand. The results are shown graphically in FIG. 10.

It is claimed:

1. A ribozyme targeted to the second GUC of human CCR5 mRNA.

2. A ribozyme construct having the ribonucleotide sequence: 3'CACAGUUCAAAGCAGGUGUGCCUGAGUAGUCGUUAGAUA5'(SEQ ID NO: 4).

3. The ribozyme of claim 2, wherein one or more of the ribonucleotides outside of the catalytic region are replaced with deoxyribonucleotides.

4. The ribozyme of claim 1, wherein the ribozyme is a hammerhead ribozyme.

5. An expression vector containing a nucleic acid encoding a ribozyme of any one of claims 1, 2, 3 or 4 operatively linked to control signals that direct the expression of such nucleic acid in mammalian cells.

6. The expression vector according to claim 5 wherein the nucleic acid encoding the ribozyme is present as an insert in the expression cassette U6+19.

7. The expression vector according to claim 5 wherein the nucleic acid encoding the ribozyme is present as an insert in the expression cassette U6+27.

8. The expression vector according to claim 5 wherein the vector is an LN retroviral vector containing the MoMLV LTR promoter.

9. The expression vector according to claim 5 wherein the vector contains the adenoviral VA1 promoter.

* * * * *

UNITED STATES PATENT AND TRADEMARK OFFICE
CERTIFICATE OF CORRECTION

PATENT NO. : 6,100,087

DATED : August 8, 2000

INVENTOR(S) : John J. Rossi and Laurence Cagnon

It is certified that error appears in the above-identified patent and that said Letters Patent are hereby corrected as shown below:

Col. 5, line 24, "(SEQ. ID NO. 4)" should be --(SEQ. ID NO. 7)--.

Signed and Sealed this

First Day of May, 2001

Attest:

NICHOLAS P. GODICI

*Attesting Officer*   *Acting Director of the United States Patent and Trademark Office*

SEQUENCE LISTING

<160> NUMBER OF SEQ ID NOS: 7

<210> SEQ ID NO 1
<211> LENGTH: 39
<212> TYPE: RNA
<213> ORGANISM: Artificial Sequence
<220> FEATURE:
<221> NAME/KEY: misc_RNA
<222> LOCATION: (1)..(39)
<220> FEATURE:
<223> OTHER INFORMATION: Description of Artificial Sequence: anti-CCR5 Rz

<400> SEQUENCE: 1
auagauugcu gaugaguccg uguggacgaa acuugacac                    39

<210> SEQ ID NO 2
<211> LENGTH: 18
<212> TYPE: RNA
<213> ORGANISM: Homosapiens
<220> FEATURE:
<221> NAME/KEY: mRNA
<222> LOCATION: (1)..(18)

<400> SEQUENCE: 2
gugucaaguc caaucuau                                           18

<210> SEQ ID NO 3
<211> LENGTH: 25
<212> TYPE: RNA
<213> ORGANISM: Artificial Sequence
<220> FEATURE:
<221> NAME/KEY: misc_RNA
<222> LOCATION: (1)..(25)
<220> FEATURE:
<223> OTHER INFORMATION: Description of Artificial Sequence:  U6plus19

<400> SEQUENCE: 3
gugcucgcuu cggcagcacg ucgac                                   25

<210> SEQ ID NO 4
<211> LENGTH: 33
<212> TYPE: RNA
<213> ORGANISM: Artificial Sequence
<220> FEATURE:
<221> NAME/KEY: misc_RNA
<222> LOCATION: (1)..(33)
<220> FEATURE:
<223> OTHER INFORMATION: Description of Artificial Sequence: U6plus27

<400> SEQUENCE: 4
gugcucgcuu cggcagcaca uauacuaguc gac                          33

<210> SEQ ID NO 5
<211> LENGTH: 26
<212> TYPE: RNA
<213> ORGANISM: Artificial Sequence
<220> FEATURE:
<221> NAME/KEY: misc_RNA
<222> LOCATION: (1)..(26)
<220> FEATURE:
<223> OTHER INFORMATION: Description of Artificial Sequence: U6[@0003]'end

<400> SEQUENCE: 5
ucuagagcgg acuucggucc gcuuuu                                  26

<210> SEQ ID NO 6

```
<211> LENGTH: 160
<212> TYPE: RNA
<213> ORGANISM: Adenovirus
<220> FEATURE:
<221> NAME/KEY: mRNA
<222> LOCATION: (1)..(160)

<400> SEQUENCE: 6
gggcacucuu ccguggucug guggauaaau ucgcaagggu accauggcgg acgaccgggg      60
uucgaacccc gcauccggcc guccgccgug auccaugcgg uuaccgcccg cgugucgaac     120
ccaggugugc gacgucagac aacgggggag cgcuccuuuu                          160

<210> SEQ ID NO 7
<211> LENGTH: 227
<212> TYPE: RNA
<213> ORGANISM: Artificial Sequence
<220> FEATURE:
<223> OTHER INFORMATION: Description of Artificial Sequence: VA1-CCR5 Rz
<220> FEATURE:
<221> NAME/KEY: misc_RNA
<222> LOCATION: (1)..(227)

<400> SEQUENCE: 7
gggcacucuu ccguggucug guggauaaau ucgcaagggu aucauggcgg acgaccgggg      60
uucgaacccc ggauccggcc guccgccgug auccaugcgg uugcggccgc gucgacauag     120
auugcugaug aguccgugug gacgaaacuu gacacucuag agcggccgca ccgcccgcgu     180
gucgaaccca ggugugcgac gucagacaac gggggagcgc uccuuuu                  227
```